US006037303A

United States Patent [19]

Peratello et al.

[11] Patent Number: 6,037,303

[45] Date of Patent: Mar. 14, 2000

[54] SUPERACID CATALYST FOR THE HYDROISOMERIZATION OF N-PARAFFINS AND PROCESS FOR ITS PREPARATION

[75] Inventors: Stefano Peratello, Nova Milanese; Angela Carati, S. Giuliano Milanese, both of Italy

[73] Assignee: Eniricerche S.p.A., S. Donato Mil.se, Italy

[21] Appl. No.: 09/019,795

[22] Filed: Feb. 6, 1998

[30] Foreign Application Priority Data

Feb. 20, 1997 [IT] Italy ................................ MI97A0358

[51] Int. Cl.[7] ............................ B01J 27/053; B01J 21/06

[52] U.S. Cl. .......................... 502/217; 502/223; 502/339; 502/349

[58] Field of Search .................................... 502/217, 223, 502/339, 349

[56] References Cited

U.S. PATENT DOCUMENTS 5,786,294 7/1998 Sachtler et al. ......................... 502/349

FOREIGN PATENT DOCUMENTS 0 520 543 12/1992 European Pat. Off. .

0520543 12/1992 European Pat. Off. ....... B01J 27/053

WO 97/43040 11/1997 WIPO .

OTHER PUBLICATIONS

Tichit et al, One step sol–gel synthesis of sulfated–zirconia catalysts, Catalysis Letters 38, pp. 109–113, 1996, no month.

Qisheng Huo, et al., Chemistry of Materials, vol. 6, No. 8, pp. 1176–1191, "Organization of Organic Molecules with Inorganic Molecula Species into Nanocomposite Biphase Arrays", Aug. 1, 1994.

D. Tichit, et al., Catalysis Letters, vol. 38, pp. 109–113, Dec. 28, 1995, "One–Step Sol–Gel Synthesis of Sulfated–Zirconia Catalystas", 1996.

*Primary Examiner*—John F. Niebling

*Assistant Examiner*—Alexander G. Ghyka

*Attorney, Agent, or Firm*—Oblon, Spivak, McClelland, Maier & Neustadt, P.C.

[57] ABSTRACT

A superacid catalyst comprising zirconium oxide having a purely tetragonal crystalline phase structure and whose surface has sulfate groups thereon in a quantity corresponding to the total coverage of the surface of the zirconium oxide by a monolayer of said sulfate groups, the zirconium oxide having a porosimetric distribution consisting of at least 70% of pores having a diameter ranging from 1–4 nm.

15 Claims, 7 Drawing Sheets

TOTAL CONVERSION N-HEPTANE (%)

100, 90, 80, 70, 60, 50, 40, 30, 20, 10, 0

A

B 100 120 140 160 180 200 220 240

Tr (°C)

TOT.% CONV.
SEL ISO C7 %
SEL.CRACK. %
A
B
C
%
100
80
60
40
20
0
5
10
15
20
25
30
35
1/WHSV (h)

TOTAL CONVERSION N-HEPTANE (%)
100
90
80
70
60
50
40
30
20
10
0
100
120
140
160
180
200
220
240
Tr (°C)
A
B

SUPERACID CATALYST FOR THE HYDROISOMERIZATION OF N-PARAFFINS AND PROCESS FOR ITS PREPARATION

BACKGROUND OF THE INVENTION

1. Field of the Invention

The present invention relates to a superacid catalyst based on sulfated zirconium oxide, the process for its preparation and its use in acid-catalyzed processes and in the hydroisomerization of n-paraffins.

2. Description of the Background

Catalysts based on sulfated oxides of zirconium, titanium, iron having superacid characteristics, according to the definition of Gillespie, as described for example by K. Arata, Adv. Catal., 37, 165, 1990, are known in the art. These superacid catalysts are usually prepared by means of an articulate synthesis comprising numerous steps. For example sulfated zirconia ($ZrO_2/SO_4^{-2}$) is generally prepared as follows:

1) precipitation of fresh zirconia hydroxide;
2) drying;
3) impregnation with a sulfating agent;
4) calcination.

Step (3) can be carried out in different ways: via wet inbibition point, as described in EP 520 543, by treatment with a gaseous stream of $H_2S$ or $SO_2$, as described by J. R. Shon, H. W. Kim, in J. Mol. Catal., 52, (1989), 361, or by treatment in solution (R. Le Van Mao, S. Xiao and T. Si Le, Catal. Lett., 35 (1995), 107; D. Farcasiu, J. Qi Li, in appl. Cat. A, 128 (1995), 97). All the steps of this preparation are critical: zirconium precursor, drying temperature, sulfating agent, concentration of the solution of sulfating agent used, temperature and calcination time. It is therefore difficult to control and reproduce the synthesis. Simplified syntheses of $ZrO_2/SO_4^{2-}$ comprising a single synthesis step, have recently been effected. For example H. Arata et al. use $Zr(SO_4)_2$ as precursor (Bull Chem. Soc. Jpn., (1990), 244): this method however does not allow the content of sulfur and its dispersion to be controlled. U. Ciesla et al. precipitate the zirconium hydroxide in the presence of alkyl sulfonates or sulfonates (EUROPACAT II Congress 3–8 September 1995). The crystallization of the amorphous phase starts at very high temperatures, over 650° C.

Another synthesis method in a single step is based on the gelification of $Zr(OC_3H_7)_4$ dispersed in propanol, in an acid environment of $HNO_3/H_2SO_4$. The material, before being calcined, must be dried under supercritical conditions (D. A. Ward, E. I. Ko, J. Cat., 150, (1994), 18).

In D. Tichit et al., Catal. Let., 38 (1996) 109–113, $Zr(OC_3H_7)_4$ dispersed in propanol, is gelified in an acid environment of $H_2SO_4$. The materials obtained after calcination at 650° C. prove to consist of tetragonal phase associated with small quantities of monocline phase.

SUMMARY OF THE INVENTION

It has now been found that it is possible, by means of a process in a single reaction step, to obtain a catalyst of sulfated zirconia with particular porosity characteristics and with high acid properties.

A first object of the present invention therefore relates to a superacid catalyst comprising zirconium oxide on the surface of which there are sulfate groups, in a quantity corresponding to the total coverage of the surface of zirconium oxide by a monolayer of said sulfate groups, characterized by a porosimetric distribution consisting of at least 70% of pores with a diameter ranging from 1 to 4 nm.

DETAILED DESCRIPTION OF THE PREFERRED EMBODIMENTS

According to a preferred aspect the catalytic material of the present invention can additionally contain a noble metal, preferably platinum, in a quantity ranging from 0.1 to 3% by weight.

Figure 1:
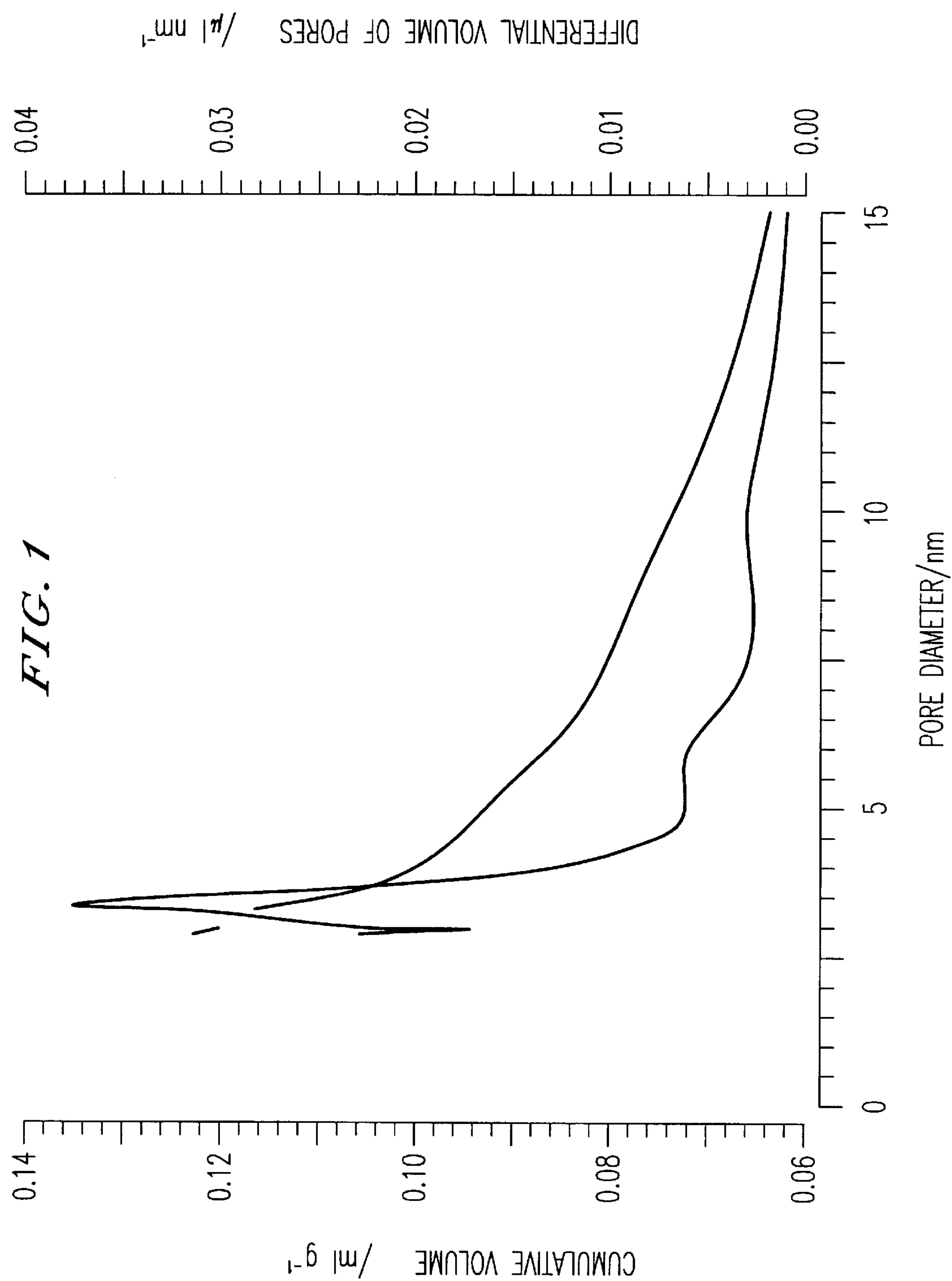
FIG. 1 shows the cumulative volume and the differential volume of the pores of the catalyst of Example 1 in relation to pore diameter.

The presence of superacid sites in the material of the present invention was verified by absorption of pyridine and analysis of the FT-IR spectrum. It has in fact been made known by K. Tanabe et al., Successful Design of Catalysts, T. Inui Ed., (1988), 616, that sulfated zirconia has an intense IR band at about 1370 $cm^{-1}$, due to the asymmetrical stretching of the S═O group. The absorption of pyridine causes a consistent shift of this signal and the entity of this shift is correlated to the superacid strength of the material and its catalytic properties. The material of our invention showed a shift between 50 and 60 $cm^{-1}$ against a maximum value cited in literature of 50 $cm^{-1}$.

The materials of the present invention are completely crystalline to X rays and consist of crystallites of tetragonal zirconia with dimensions of less than 300 Å, generally between 50 and 150 Å. The porosity is between 0.1 and 0.3 $cm^3/g$. The surface area of these materials is greater than 30 $m^2/g$, preferably between 60 and 120 $m^2/g$.

The content of sulfates can be determined by chemical analysis and corresponds to the theoretical value which can be calculated for the whole coverage of the surface of the zirconia by a monolayer of sulfate groups, as described by P. Nascimento et al., in "New Frontiers in Catalysis", Proceedings of the 10th International Congress on Catalysis (L. Guczi et al. EDS.) p. 1185, Elsevier (1993). For a surface area included within the preferred values previously indicated, the content of sulfur in the catalyst, corresponding to a monolayer of sulfate groups, is between 1 and 3% by weight.

The sulfate groups are attached to the zirconia by the hydroxyls present on its surface and therefore the possibility of obtaining a monolayer of sulfates, corresponding to the maximum acidity of the material, is linked to the presence on the surface of the zirconia of a sufficient number of hydroxyls. The particular process we use for preparing the materials of the present invention causes the formation of a sufficient quantity of hydroxyls, it is a process with only one reaction step and determines the porosity characteristics claimed herein. A second object of the present invention therefore relates to a process for the preparation of the materials described above which comprises:

(a) the hydrolysis in an alkaline environment of a hydrolyzable zirconium compound in the presence of an alcohol ROH, a tetra-alkylanmonium (TAA) hydroxide and sulfuric acid;

(b) drying the resulting product and its calcination at a temperature ranging from 250 to 650° C.

In step (a) of the process of the present invention, the tetra-alkylammonium hydroxide is selected from hydroxides of the type $R_1R_2R_3R_4NOH$, wherein $R_1$, $R_2$, $R_3$ and $R_4$ are the same or different and are alkyl groups preferably comprising from 1 to 6 carbon atoms; the hydrolyzable derivative of zirconium is selected from alkoxyderivatives, nitrate, sulfate, and is preferably tetrapropylorthozirconate. The sulfuric acid is used in an aqueous solution with a concentration ranging from 0.01 to 10 M.

The alcohol used in step (a) has the formula ROH, wherein R is an alkyl with a number of carbon atoms ranging from 1 to 6, and is preferably propanol. The molar ratios of the mixture of step (a) are the following:

TAA/Zr=0.05–0.25

ROH/Zr=10–100

$H_2SO_4$/Zr=0.1–0.5

$H_2O$/Zr=2–100

According to a preferred aspect the compound of zirconium is dispersed in the alcohol ROH and the tetra-alkylammonium hydroxide in aqueous solution, preferably tetrapropylammonium hydroxide, is added to this solution; the resulting solution is left under stirring for several hours before proceeding with the addition of the sulfuric acid solution. The resulting dense slurry, which must have a basic pH, is left under stirring for a period of 2–20 hours.

In step (b) the resulting product, after possible concentration, is dried and then calcined.

According to a preferred aspect, the catalytic material of the present invention may additionally contain a noble metal, preferably platinum, in a quantity ranging from 0.1 to 3% by weight. These catalysts containing a noble metal are prepared by subjecting the material obtained in step (b) to impregnation, by means of the "wet inbibition" method which is well-known in literature, with an aqueous solution of a compound of noble metal, preferably platinum, to deposit a quantity of noble metal of 0.1 to 3% by weight. Hexachloroplatinic acid and ammoniacal complexes of tetravalent platinum are preferred for the purpose.

The drying is then carried out at a temperature ranging from 80° to 150° C. followed by calcination at a temperature ranging from 400° to 600° C.

The catalyst based on sulfated zirconia of the present invention is a superacid solid and can therefore be used in acidcatalyzed reactions. The materials of the present invention which additionally contain a noble metal are bifunctional catalysts which can be used in hydroisomerization processes of n-paraffins to convert these hydrocarbons with a linear chain into hydrocarbons with a branched chain. According to a preferred aspect of the present invention in particular light paraffins can be subjected to hydroisomerization to obtain hydrocarbons with a branched chain having a higher octane number, which can be used as fuels.

A particular aspect of the present invention therefore relates to a hydroisomerization process of n-paraffins having from 4 to 10 carbon atoms, characterized in that the n-paraffin, or mixture of n-paraffins, is put in contact, under hydroisomerization conditions, with a superacid catalyst comprising zirconium oxide on the surface of which there are sulfate groups, in a quantity corresponding to the total coverage of the surface of zirconium oxide by a monolayer of said sulfate groups, characterized by a porosimetric distribution consisting of at least 70% of pores with a diameter ranging from 1 to 4 nm, containing a noble metal in a quantity ranging from 0.1 to 3% by weight.

In particular, by subjecting $C_5$–$C_6$ n-paraffins, or a mixture of these, such as the Light straight run fraction deriving from cracking, to hydroisomerization, light fuels are obtained with a high octane number. By subjecting, on the other hand, $C_7$–$C_9$ n-paraffins, or their mixtures, to hydroisomerization, it is possible to obtain heavy fuels with a high octane number. The bifunctional catalysts of the present invention are very active and consequently give high performances both in terms of conversion and selectivity to hydroisomerization products, particularly with respect to the by-products of the competitive cracking process, also at much lower temperatures than those which must be adopted for the zirconia sulfates with noble metal of the prior art.

The process is carried out in the presence of hydrogen, at a temperature ranging from 25° to 300° C., preferably from 50° to 130° C., and at a pressure ranging from 5 to 80 bars, preferably from 20 to 50 bars. The noble metal is preferably platinum. The WHSV space velocity ($hours^{-1}$), expressed as g paraffin/g cat. hours, is between 0.01 and 1, and the molar ratio hydrogen/paraffin is between 5 and 30.

According to another aspect of the present invention, these bifunctional catalysts can be used in hydroisomerization processes of waxes (n-paraffins with a number of carbon atoms equal to or greater than 12) to improve their pour point and viscosity index, in order to obtain bases for lubricating oils.

EXAMPLE 1

33 g of $Zr(OC_3H_7)_4$ at 70% by weight in propanol and 5 g of tetrapropylammonium hydroxide at 40% by weight in aqueous solution are added to 182 g of n-$C_3H_7OH$. After two hours of aging under stirring, 25 g of an aqueous solution of $H_2SO_4$ 0.44 M are added. The mixture is left under stirring for four hours at room temperature, then for a further 4 hours at 60° C. The sample is dried for 8 hours at 100° C. and is then calcined for 5 hours at 550° C. The material obtained after calcination consists of a pure tetragonal phase with crystallites having a diameter of 85 Å, with a surface area of 103 $m^2/g$, a pore volume of 0.162 $cm^3/g$ with a distribution of the pore diameter on 3.5 nm. FIG. 1 shows the cumulative volume and the differential volume of the pores in relation to the pore diameter. The final content of sulfur determined by chemical analysis is 1.7% which corresponds to the total surface coverage of monolayer of sulfate groups. FT-IR analysis shows a shift of 60 $cm^{-1}$ of the signal at 1370 $cm^{-1}$ following the interaction with pyridine.

EXAMPLE 2

10 g of the material prepared in example 1 are impregnated using the wet inbibition technique with 1.6 ml of an aqueous solution of $H_2PtCl_6$ containing 0.031 g of Pt per ml. The resulting product is dried at 100° C. and calcined at 550° C. A catalyst is obtained with a total content of Pt of 0.5% by weight.

EXAMPLE 3

10 g of the material prepared in example 1 are impregnated using the wet inbibition point technique with 1.6 ml of an aqueous solution of $H_2PtCl_6$ containing 0.063 g of Pt per ml. The resulting product is dried at 100° C. and calcined at 550° C. A catalyst is obtained with a total content of Pt of 1% by weight.

EXAMPLE 4

10 g of the material prepared in example 1 are impregnated using the wet inbibition point technique with 1.6 ml of an aqueous solution of $H_2PtCl_6$ containing 0.125 g of Pt per ml, as described in example 2. The resulting material has a total content of Pt of 2% by weight.

EXAMPLE 5

The synthesis of example 1 is repeated, operating without tetrapropylammonium oxide.

The zirconium sulfate obtained after calcination consists of a mixture of tetragonal phase (96%) of a monocline phase (4%) with crystallites having dimensions of about 100 Å. It has a surface area of 93 $m^2/g$, a pore volume of 0.27 $cm^3/g$, and a distribution of the enlarged porosity ranging from 60 to 300 Å of radius. The final content of sulfur is 1.7%.

10 g of the material thus prepared are impregnated using the wet inbibition point technique with 1.5 ml of an aqueous solution of $H_2PtCl_6$ containing 0.033 g of Pt per ml. The resulting material has a total content of Pt of 0.5% by weight.

EXAMPLE 6

The synthesis of example 1 is repeated, operating without sulfuric acid. The content of tetrapropylammonium hydroxide was doubled to allow the gelation of the mixture. The material obtained after calcination has a surface area of 5 $m^2/g$.

EXAMPLE 7

A sulfated zirconia having a surface area of 180 $m^2/g$ and a sulfur content of 1.7% was prepared in accordance with example 12 of EP 520543. 10 g of the material thus prepared are impregnated using the wet inhibition point technique with an aqueous solution of $H_2PtCl_6$ containing 0.038 g of Pt per ml. The resulting material has a total Pt content of 0.5% by weight.

EXAMPLE 8

(Catalytic Test)

A sample of catalyst synthesized as described in example 2 is charged into a fixed-bed tubular reactor and tested in the hydroisomerization reaction of n-heptane, under the following operating conditions:

T=130° C.

$H_2$ P=50 bars $H_2$/n-$C_7$=18 mol/mol.

Figure 2:
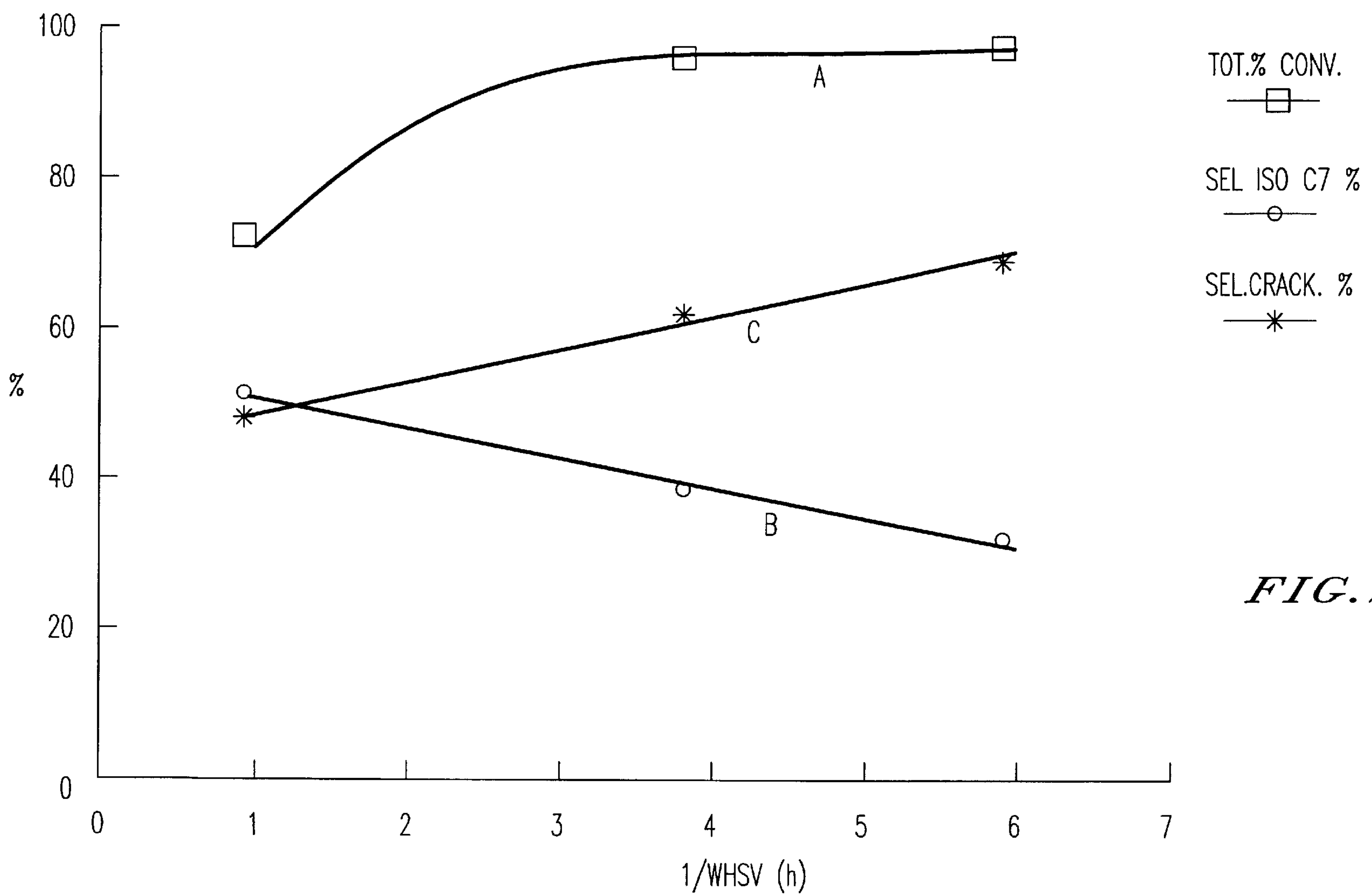
FIG. 2 shows the conversion of n-heptane, selectivity to isomerized products and selectivity to cracked products over the catalyst of Example 2 at 130° C.

FIG. 2 shows the conversion of n-heptane (curve A) and the selectivity to isomerization products (curve B) in relation to the contact time expressed as 2/WHSV. The WHSV parameter is calculated as (g of n-$C_7$)/(hours.g of catalyst). The hydroisomerization products obtained are:

methylhexanes, dimethylpentanes and trimethylbutanes.

FIG. 2 also shows the selectivity to cracking products (curve C).

As can be seen from FIG. 2, a conversion of practically 100% is reached with the catalysts of the present invention, with selectivity values to hydroisomerization ranging from 30 to 50%, at a temperature of 130° C., whereas the sulfated zirconias with Pt of the prior art are only active at much higher temperatures.

EXAMPLE 9

A sample of catalyst synthesized as described in example 2 is charged into a fixed-bed tubular reactor and tested in the hydroisomerization reaction of n-heptane, under the following operating conditions:

T=100° C.

$H_2$ P=50 bars $H_2$/n-$C_7$=18 mol/mol.

Figure 3:
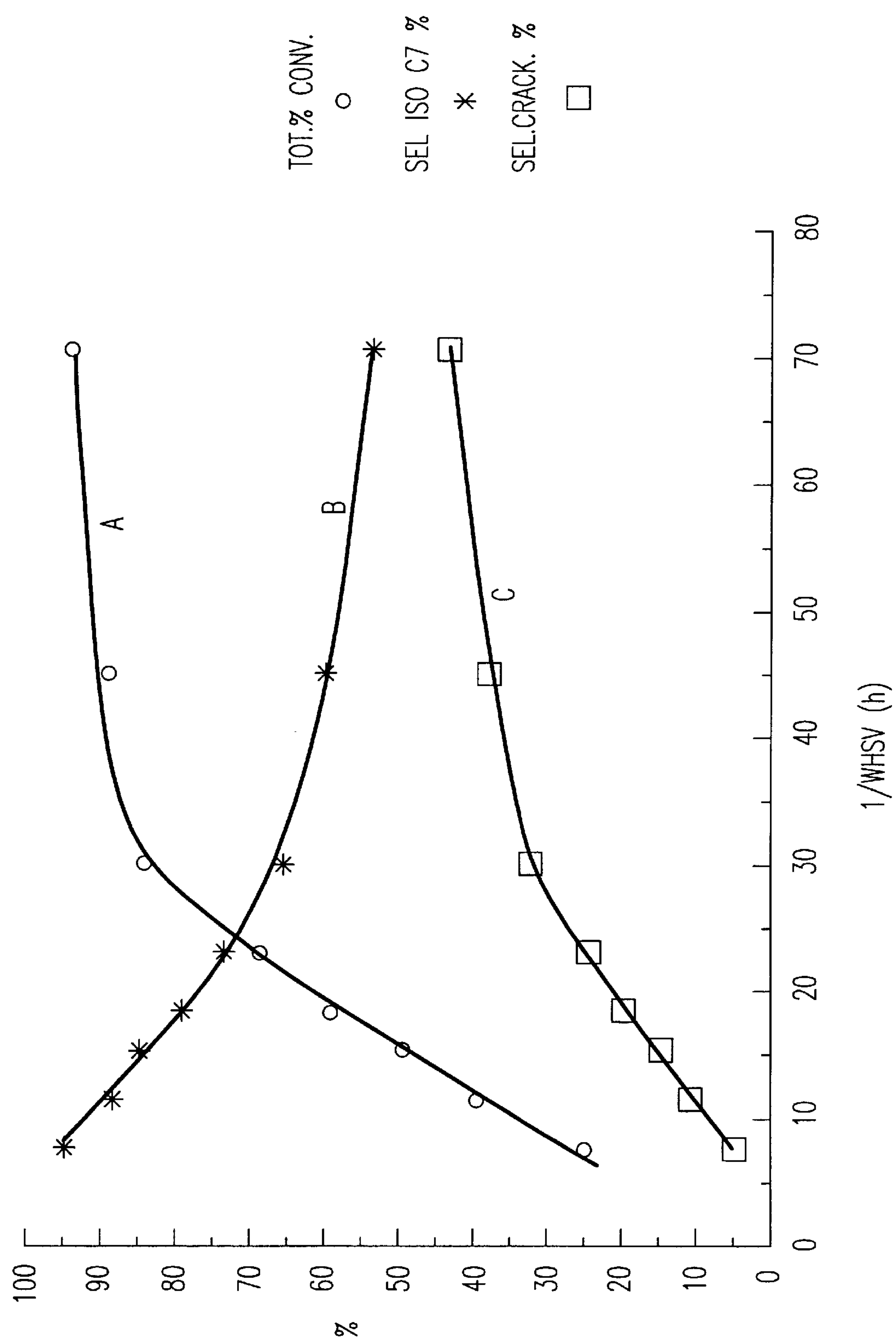
FIG. 3 shows the conversion of n-heptane, selectivity to isomerized products and selectivity to cracked products over the catalyst of Example 2 at 100° C.

FIG. 3 shows the conversion of n-heptane (curve A), the selectivity to isomerization (curve B) and the selectivity to cracking (curve C) in relation to the contact time expressed as 1/WHSV. The WHSV parameter is calculated as (g of n-$C_7$)/(hours.g of catalyst). Operating at a lower temperature with respect to the previous example, it is possible to reach a conversion of practically 100% and selectivity values to isomerization products are obtained ranging from 55 to 95%.

EXAMPLE 10

A sample of catalyst synthesized as described in example 3 is charged into a fixed-bed tubular reactor and tested in the hydroisomerization hydrocracking reaction of n-heptane, under the following operating conditions:

T=130° C.

$H_2$ P=50 bars $H_2$/n-$C_7$=18 mol/mol.

Figure 4:
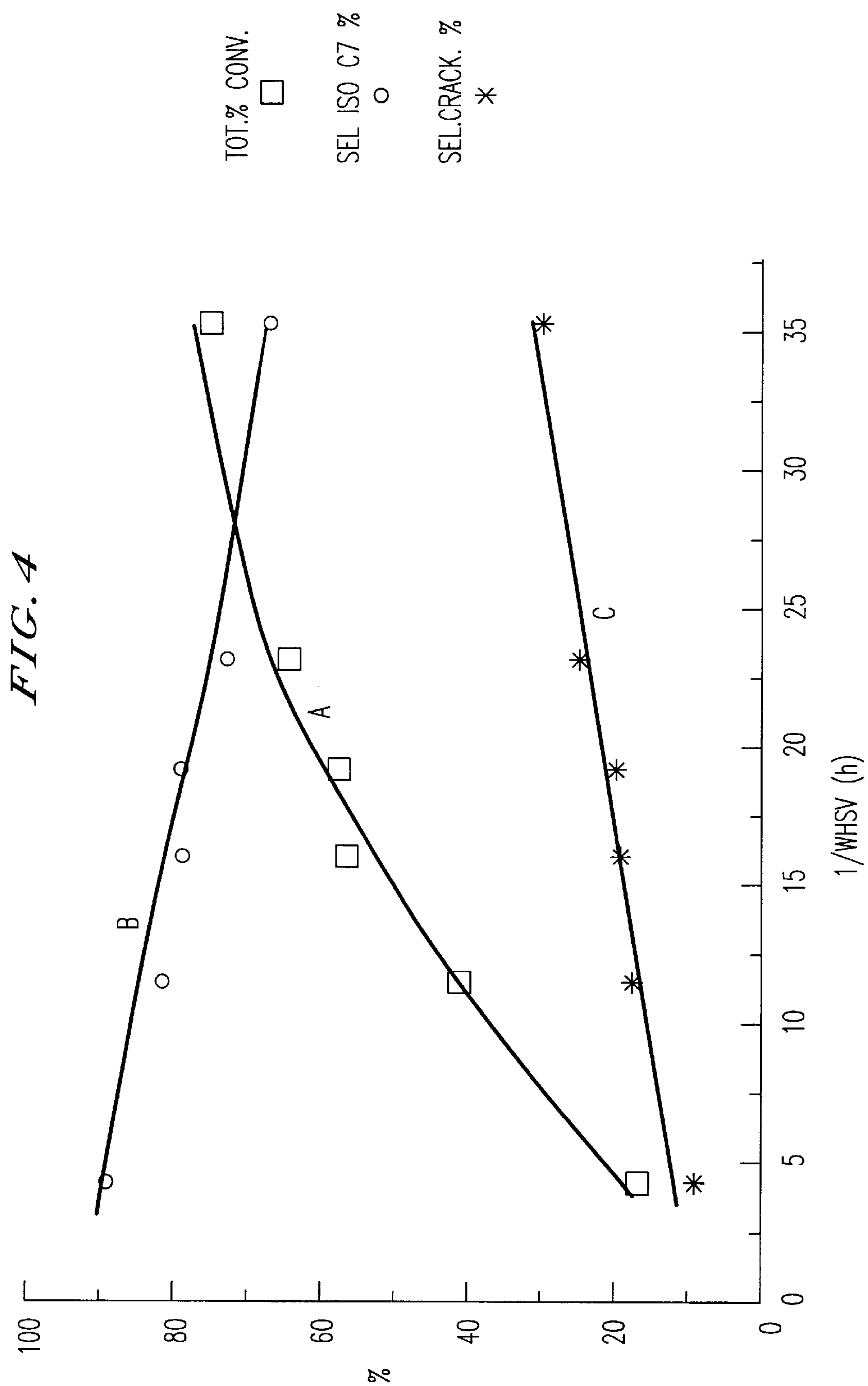
FIG. 4 shows the conversion of n-heptane, selectivity to isomerized products and selectivity to cracked products over the catalyst of the invention of Example 3 at 130° C.

FIG. 4 shows the total conversion of n-heptane (curve A), the selectivity to isomerization (curve B) and the selectivity to cracking (curve C), in relation to the contact time expressed as 1/WHSV. The WHSV parameter is calculated as (g of n-$C_7$)/(hours.g of catalyst). An increase in the content of platinum, with respect to the catalyst of the previous examples gives excellent results in terms of conversion and selectivity to isomerization products.

EXAMPLE 11

A traditional sulfated zirconia prepared as described in example 7 is compared with the material according to our invention of example 2.

The operating conditions of the catalytic test are:

$H_2$ P=50 bars $H_2$/n-$C_7$=18 mol/mol.

WHSV=0.53 $hours^{-1}$.

Figure 5:
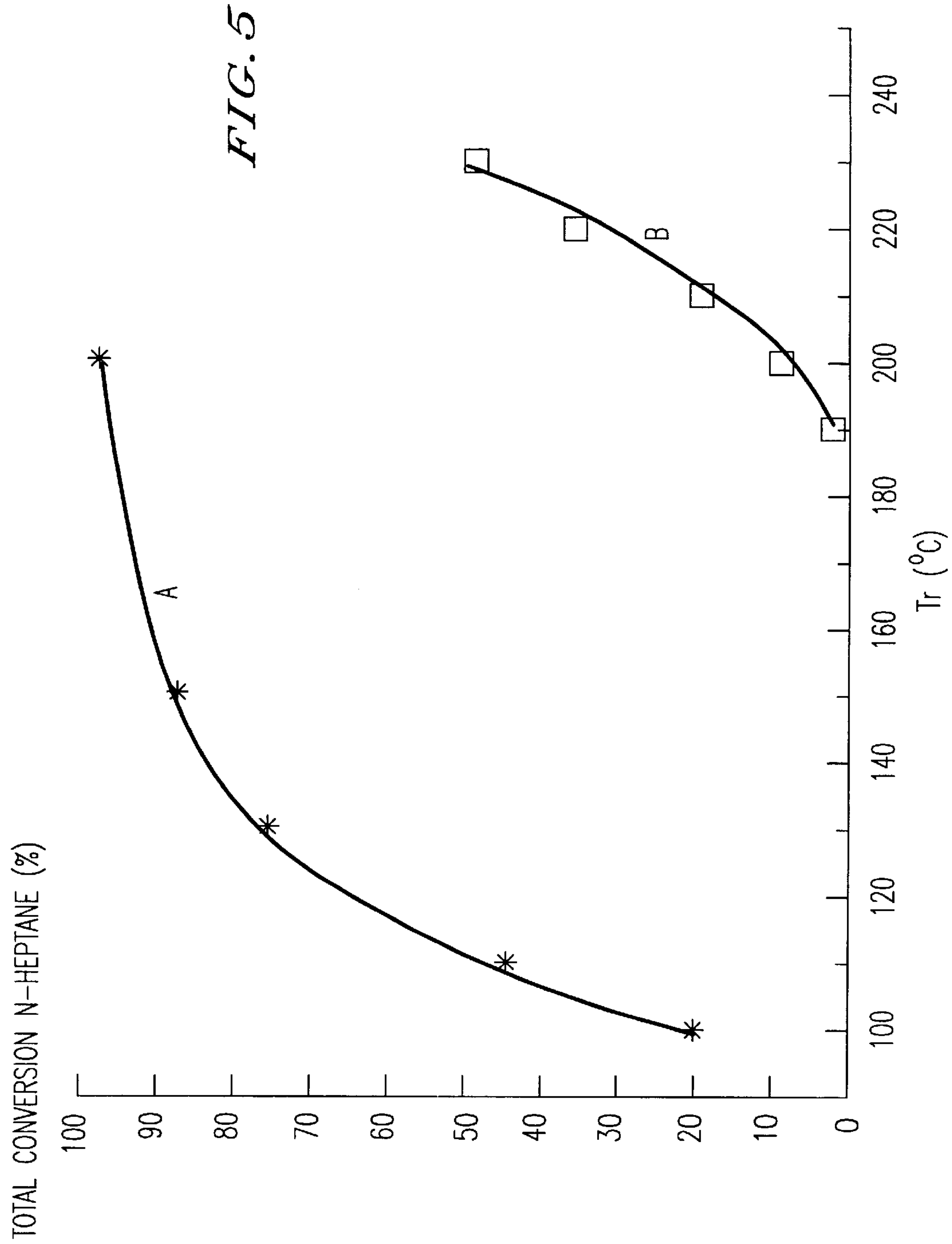
FIG. 5 shows the relationship of reaction temperature (Tr) to conversion values of n-heptane over the catalyst of the invention of Example 2 and the catalyst of Example 7 representing a catalyst embodiment of Example 12 of EP 520543.

FIG. 5 shows, in relation to the reaction temperature (Tr), the conversion values which are obtained with the catalyst of example 2 (curve A) and the conversion values which are obtained with the catalyst of example 7 (curve B): the greater activity of the catalysts of the present invention with respect to the catalysts of the prior art is evident, a high activity which is also observed at much lower temperatures with respect to those requested by the catalysts based on tradition sulfated zirconia.

EXAMPLE 12

A sulfated zirconia prepared according to example 5, without tetrapropylammonium hydroxide, is compared with the material according to our invention of example 2.

The operating conditions of the catalytic test are:

$H_2$ P=50 bars $H_2$/n-$C_7$=18 mol/mol.

WHSV=0.53 hours$^{-1}$.

Figure 6:
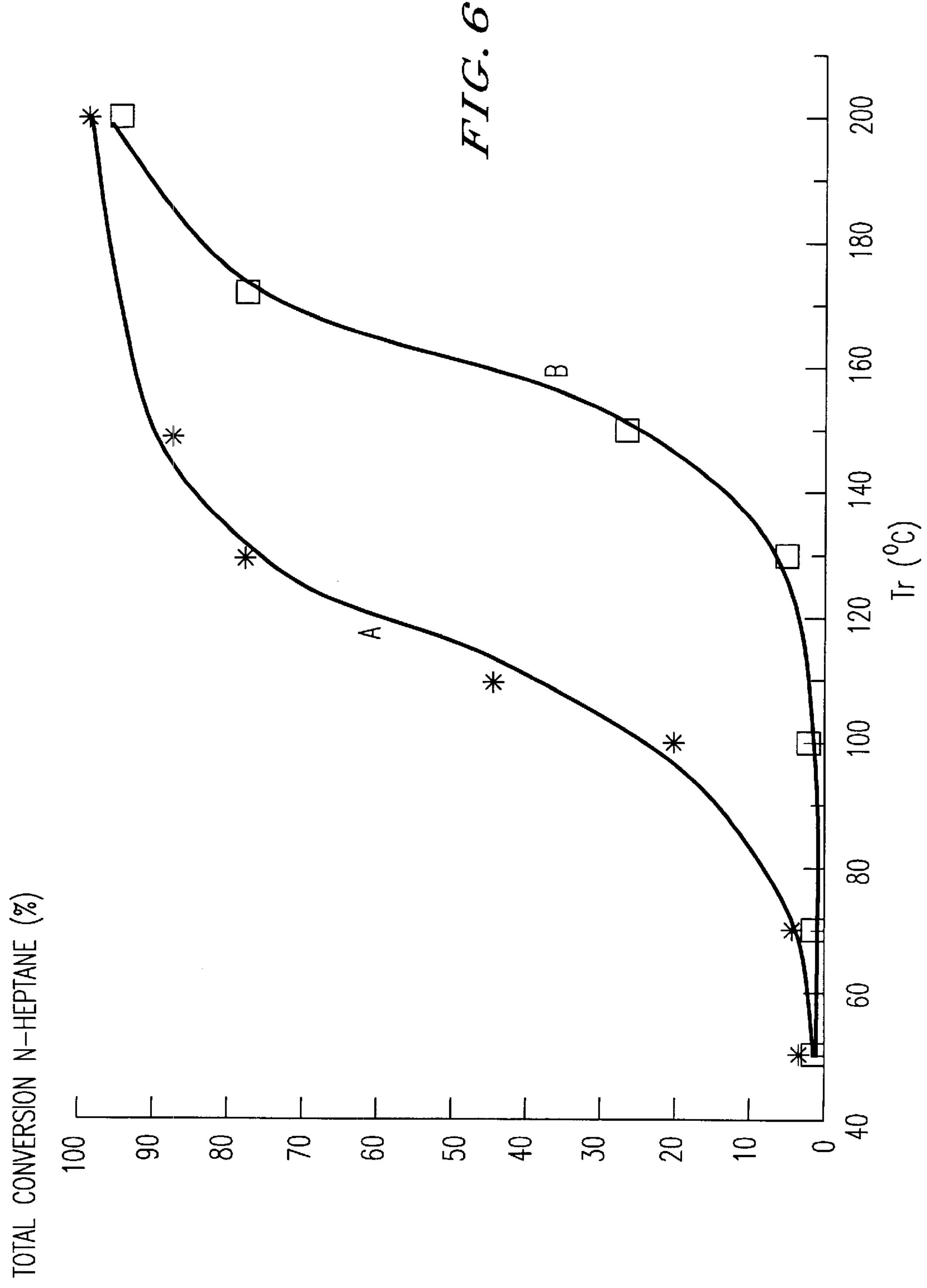
FIG. 6 shows the relationship of reaction temperature (Tr) to conversion values of n-heptane over the catalyst of the invention of Example 2 and the comparative catalyst of Example 5 (prepared without tetrapropylammonium hydroxide)

FIG. 6 shows, in relation to the reaction temperature (Tr), the conversion values which are obtained with the catalyst of example 2 (curve A) and the conversion values which are obtained with the catalyst of example 5 (curve B): the catalyst prepared without tetrapropylammonium hydroxide is clearly less active than the catalyst of our invention.

EXAMPLE 13

A sample of catalyst synthesized as described in example 4 is charged into a fixed-bed tubular reactor and tested in the hydroisomerization reaction of n-heptane, under the following operating conditions:

T=130° C.

$H_2$ P=50 bars $H_2$/n-$C_7$=18 mol/mol.

Figure 7:
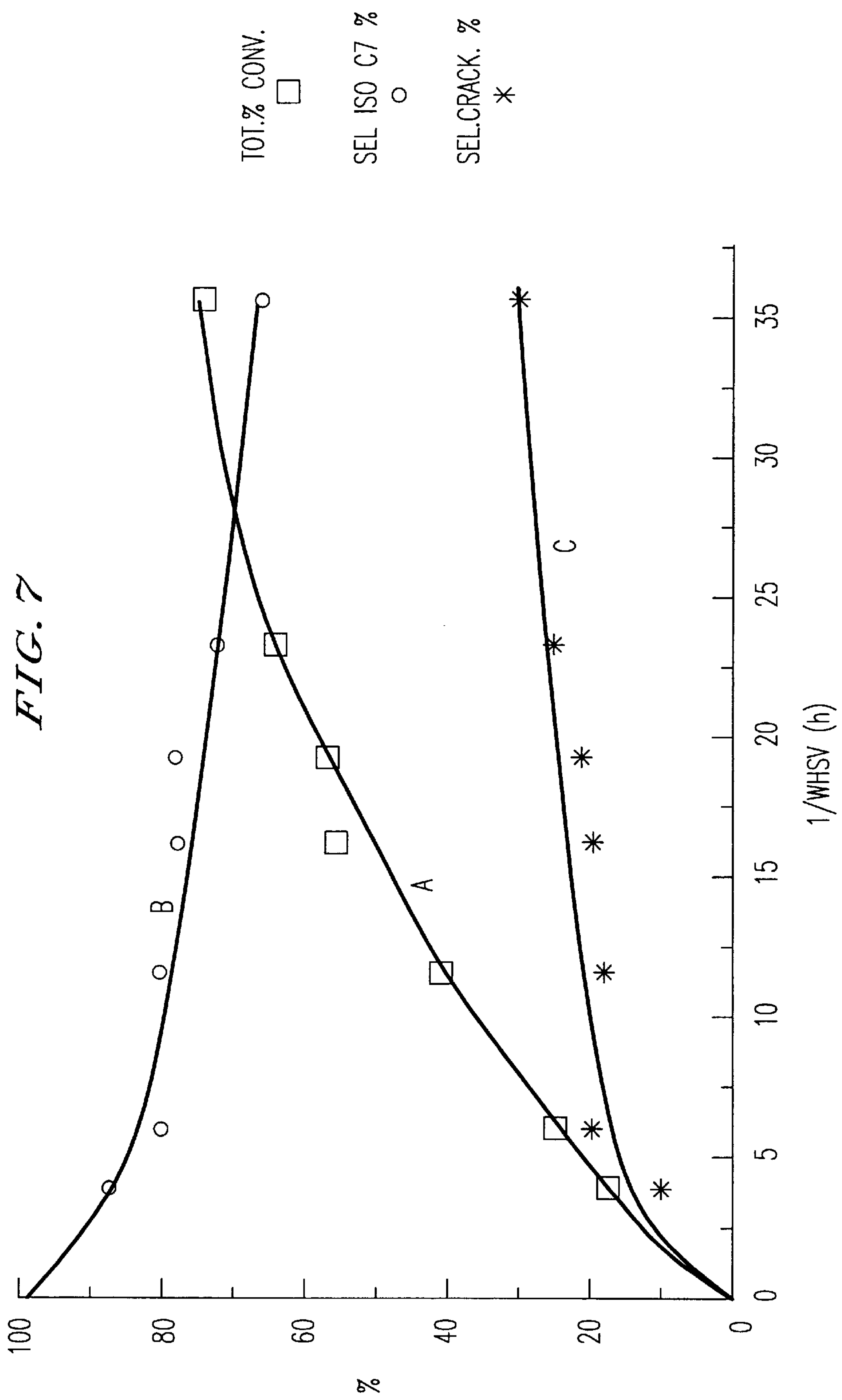
FIG. 7 shows the conversion of n-heptane, selectivity to isomerized products and selectivity to cracked products over the catalyst of Example 4 at 130° C.

FIG. 7 shows the total conversion of n-heptane (curve A), the selectivity to isomerization (curve B) and the selectivity to cracking (curve C), in relation to the contact time expressed as 1/WHSV.

We claim:

1. A superacid catalyst comprising zirconium oxide having a purely tetragonal crystalline phase structure and whose surface has sulfate groups thereon in a quantity corresponding to the total coverage of the surface of zirconium oxide by a monolayer of said sulfate groups, the zirconium oxide catalyst having a porosimetric distribution consisting of at least 70% of pores with a diameter ranging from 1–4 nm.

2. The catalyst according to claim 1, which contains a noble metal in a quantity ranging from 0.1–3% by weight.

3. The catalyst according to claim 2, wherein said noble metal is platinum.

4. The catalyst according to claim 1, wherein the surface of said zirconium oxide has an area ranging from 60–120 $m^2$/g and a sulfur content by weight, based on the weight of catalyst, ranging from 1–3%.

5. A process for the preparation of the catalyst of claim 1, which comprises:

(a) hydrolyzing a hydrolyzable zirconium compound in the presence of an alcohol ROH and tetraalkylammonium (TAA) hydroxide in a basic environment and then adding sulfuric acid thereto the environment remaining basis; and (b) drying the product obtained and calcining the product at a temperature ranging from 250–650° C.

6. The process according to claim 5, wherein the tetraalkylammonium hydroxide is selected from the group consisting of hydroxides of the formula $R_1R_2R_3R_4NOH$, wherein $R_1$, $R_2$, $R_3$, and $R_4$ are each an alkyl group which are the same or different.

7. The process according to claim 6, wherein said alkyl groups contain from 1–6 carbon atoms.

8. The process according to claim 5, wherein the tetraalkylammonium hydroxide is tetrapropylammonium hydroxide.

9. The process according to claim 5, wherein the hydrolyzable zirconium compound is selected from the group consisting of zirconium alkoxy compounds, zirconium nitrate and zirconium sulfate.

10. The process according to claim 9, wherein said zirconium compound is tetrapropylorthozirconate.

11. The process according to claim 5, wherein said sulfuric acid is added to said basic environment as an aqueous solution at a concentration ranging from 0.01–10 M.

12. The process according to claim 5, wherein the alkyl group R of said alcohol has a carbon atom content ranging from 1–6.

13. The process according to claim 5, wherein the molar ratios of the components of the basic medium subject to hydrolysis are as follows:

TAA/Zr=0.05–0.25

ROH/Zr=10–100

$H_2SO_4$/Zr=0.1–0.5

$H_2O$/Zr=2–100.

14. The process according to claim 5, wherein the material of step (b) is impregnated, employing the "wet inhibition" method, with an aqueous solution of a noble metal compound, thereby depositing a quantity of noble metal ranging from 0.1–3% by weight.

15. A superacid catalyst comprising zirconium oxide consisting of a tetragonal crystal phase structure and whose surface has sulfate groups thereon in a quantity corresponding to the total coverage of the surface of zirconium oxide by a monolayer of said sulfate groups, said zirconium oxide catalyst having a porosimetric distribution consisting of at least 70% of pores with a diameter ranging from 1–4 nm.

* * * * *